(12) United States Patent
Osypka

(10) Patent No.: US 7,994,802 B2
(45) Date of Patent: Aug. 9, 2011

(54) APPARATUS FOR EXAMINING OR MONITORING PLANTS

(75) Inventor: Peter Osypka, Rheinfelden-Herten (DE)

(73) Assignee: Peter Osypka Stiftung Stiftung des Burgerlichen Rechts, Grenzach-Wyhlen (DE)

( * ) Notice: Subject to any disclaimer, the term of this patent is extended or adjusted under 35 U.S.C. 154(b) by 280 days.

(21) Appl. No.: 12/374,705

(22) PCT Filed: Aug. 8, 2007

(86) PCT No.: PCT/EP2007/006987
§ 371 (c)(1),
(2), (4) Date: Jan. 22, 2009

(87) PCT Pub. No.: WO2008/025439
PCT Pub. Date: Mar. 6, 2008

(65) Prior Publication Data
US 2009/0278555 A1 Nov. 12, 2009

(30) Foreign Application Priority Data

Sep. 1, 2006 (DE) .................. 10 2006 041 127

(51) Int. Cl.
*G01R 27/26* (2006.01)
*G01N 5/02* (2006.01)

(52) U.S. Cl. ............. 324/692; 324/71.1; 73/73
(58) Field of Classification Search .......... 324/71.1, 324/692; 73/73
See application file for complete search history.

(56) References Cited

U.S. PATENT DOCUMENTS

| 5,819,467 A | 10/1998 | Zucker | |
| 6,202,479 B1 * | 3/2001 | Frybarger | 73/73 |
| 6,870,376 B1 * | 3/2005 | Gensler | 324/664 |

FOREIGN PATENT DOCUMENTS

| DE | 3722516 | 1/1988 |
| EP | 1446999 | 2/2003 |

* cited by examiner

*Primary Examiner* — Vincent Q Nguyen
(74) *Attorney, Agent, or Firm* — Volpe and Koenig, P.C.

(57) ABSTRACT

An apparatus (1) is used to examine or monitor the state or state of health of plants (2) with the aid of a bipolar electrode (4) which uses its at least two different poles (5) to measure corresponding potentials of the plant and supply them to a detector and/or memory (7), in particular via an amplifier (9), with the result that conclusions regarding the state of, or the possible damage to, a plant (2) can be drawn from changes in the electrical signals and can ensure remedial action.

17 Claims, 4 Drawing Sheets

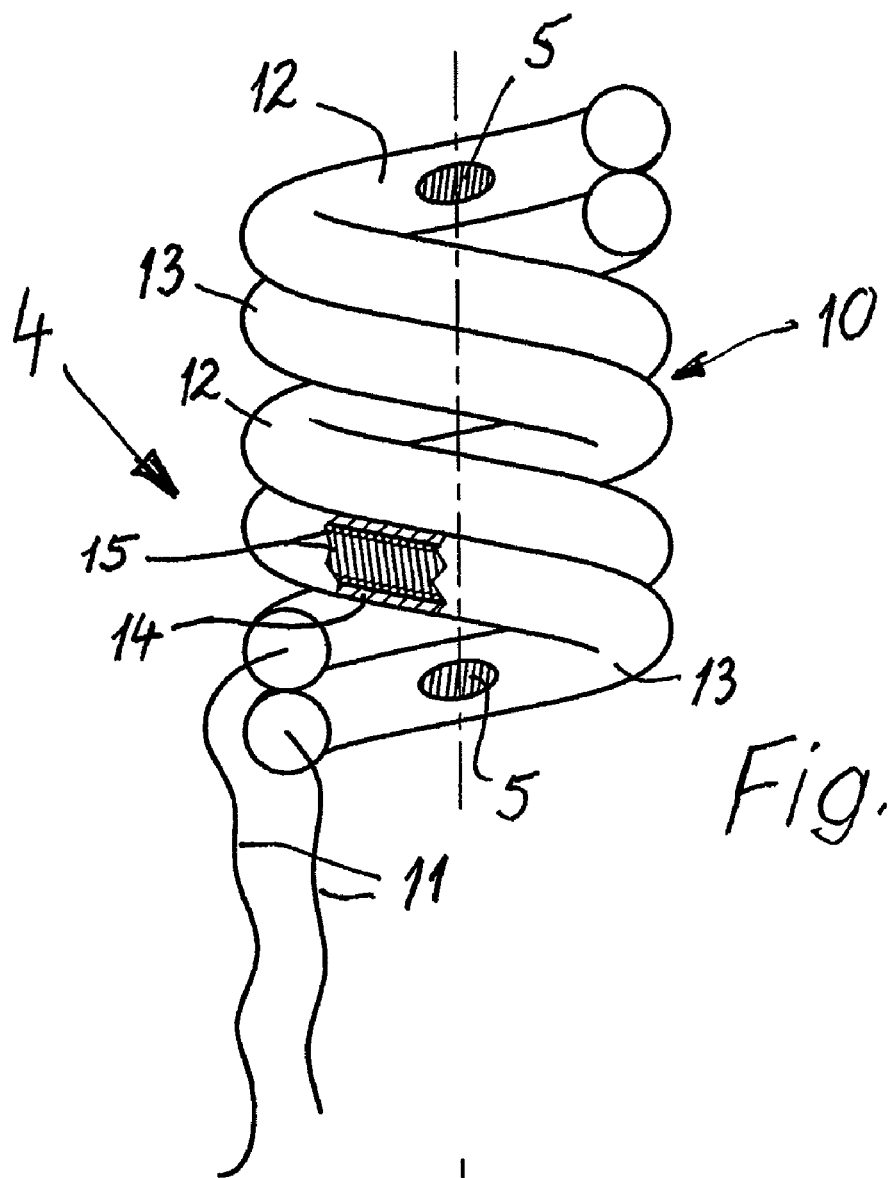
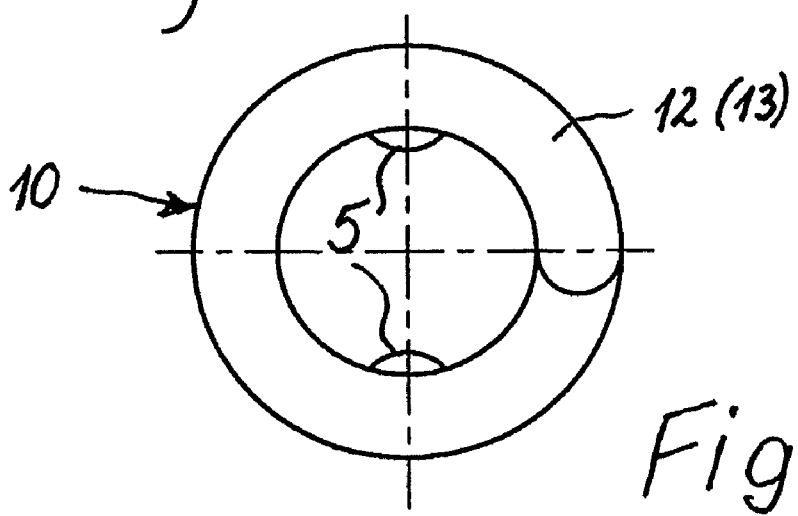
Fig. 3
Fig. 4

APPARATUS FOR EXAMINING OR MONITORING PLANTS

BACKGROUND

The invention relates to an apparatus for examining or monitoring the state or state of health of plants, in particular, for determining damage caused by environmental effects and/or by pests during the growth or lifetime of such plants.

Up until now, in particular, agricultural crops, e.g., grape vines, have been inspected visually to determine whether they have been attacked by pests or whether they exhibit phenomena deviating from normal growth and appearance. These inspections then lead to more or less all-encompassing measures, such as frequently overdimensioned spraying with pesticides, additional fertilizers, or the like. Here, the means to be applied are usually not only considerably overdimensioned, but often applied too late or at the wrong time.

SUMMARY

Therefore, there is the objective of creating an apparatus of the type noted above with which the general state or the state of health of the plant or plants can be identified in a timely way or in advance or if there is damage or the stage of damage, for example, due to pests or environmental influences.

To achieve this objective it is provided that the apparatus has a bipolar electrode that can be attached at a position or to an area of the plant where the plant outputs electrical signals and/or where an electrical potential is present or at a green position or to a green area of the plant, wherein this electrode has at least two poles that contact the plant in the position of use and that surround the attachment position(s) to the plant in the position of use at least partially or completely and that receive electrical signals or potentials of the plant. For the objective it is also provided that the bipolar electrode can be connected or is connected to a detector and/or to a memory for detecting and evaluating these potentials and for comparing potentials and signals received at different times.

The invention takes advantage of the knowledge that plants output electrical signals or have potentials that correspond to their state and that change when this state changes and when, in particular, the plant is no longer in a normal state. With the apparatus according to the invention, it is possible to monitor each plant with reference to its electrical potentials and to detect changes to these potentials in a timely way, which could point to corresponding changes, in particular, degradations in the state of the plant. Because it is known how these potentials change when the state of health of the plant changes or when the plant is attacked by pests, these changes can be used for triggering select countermeasures.

It is especially preferred when an amplifier is provided between the attachment or mounting position of the electrode to the plant and the detector and/or memory. In this way it is possible for the signals received and forwarded by the electrode to be detected and stored in a clear way with informational value.

It can be useful when several bipolar electrodes are provided and connected to a common memory. In this way, the state of several plants, for example, within a crop field or a vineyard or a garden or plant bed can be detected and monitored.

The memory can be connected wirelessly or via electrical lines to an evaluation center. Thus, the plant or the plant field can be monitored or inspected also across a large distance and optionally practically in an uninterrupted manner.

A preferred embodiment of the invention can provide the bipolar electrode has a holder or a holding end for permanent and/or detachable attachment to the plant. Thus, the bipolar electrode can stay on each plant for a long time independent of "wind and weather" and can allow its monitoring.

Here, the holder or the holding end of the electrode can be constructed for connecting to a plant as a double or twin coil in which each of the windings, arranged parallel to each other, carries or forms one of the poles of the electrode and the double coil can wrap around the measurement position on the plant at the entire extent of the attachment point, wherein the two coils or windings of the bipolar electrode forming the double coil are insulated from each other and from the surroundings and have insulation-less or stripped contact positions on their area facing the plant part or stem of the plant and arranged in the interior of the double coil as poles for directly receiving the electrical potential of the plant and/or for direct contact with the surrounded plant part. Such a coil or double coil is flexible and can expand, for example, with the increasing stem thickness of a plant. In addition, it can be easily applied, because the windings of a coil can be attached without a problem also from the side to an elongated part such as a stalk or stem. Simultaneously, such a coil or double coil can be produced economically, wherein the properties with respect to flexibility, stability, and strength can be influenced and preselected by the selection of the wire material or the wire diameter and the spring hardness and also the distance of the poles of the electrodes. Through the selection of the insulation and the stripped areas, a high security against interference due to external influences, such as, for example, condensation, is simultaneously also given.

It is especially preferred when the bipolar electrode and the holding and measurement coil belonging to it is formed from a flexible and electrically conductive material. Here, through the material selection and the selection of the dimensions of the cross sections, a weight of the bipolar electrode can be achieved that is so low that no effect on the plant in question by the attachment of this electrode is to be expected or not to a disruptive degree. This also applies especially when the selected material is biocompatible and is itself resistant to environmental influences, such as moisture, UV radiation, and temperatures.

Thus, for example, silicon, goniomer, rubber, PE, and/or PUR can be provided as the material for the insulation of the bipolar electrode and especially for the double coil or twin coil or at least one of its coils or windings.

An especially effective bipolar electrode is given when the two coils belonging to it are formed, on their side, from wire coils that are shaped in the area of the holder or attachment position on the plant to the windings of the double coil that surrounds the plant in the position of use. The individual electrodes of the bipolar electrode are thus formed from wire windings and then formed, on their side, into correspondingly larger windings adapted to the dimensions of the attachment position in the region of the attachment position to the plant. In this way, electrodes of higher flexibility and adaptability to the object to be wrapped are produced.

One configuration of the invention of very considerable and advantageous significance can be provided in that the bipolar electrode is connected directly or indirectly to a controller with which countermeasures targeted, in particular, to an attack of pests, such as the spraying of counteragents or pesticides or the administration of medicine or fertilizer can be triggered. The apparatus according to the invention can also include a corresponding controller and optionally also the container and the apparatus with which pesticides and/or fertilizers can be discharged.

For example, the detector or memory belonging to the apparatus can be connected to the controller and this can be connected to a discharge apparatus or container that contains the counteragent and has a closable opening that can be selectively opened by the controller or by its control pulses. Thus, according to the state that is detected by the bipolar electrode, the supply of counteragents can be provided selectively or even automatically when the determined measurement result is not beneficial for the plant. Here, an apparatus constructed in this way has the advantage that the effect, for example, of a pesticide can also be tested very selectively and on only a small extent of individual plants or can also be dosed very selectively and as little as possible in its application.

The container for the controlled or optionally also regulated discharge of counteragents or nutrients can be shaped so that it can be attached to or by the attachment position of the plant for the electrode or can be fixed thereto by the bipolar electrode or its holder. This produces a combination of the bipolar electrode that can also be allocated for the user in a simple way to a plant with the part with which possible reactions to unfavorable measurement results can be created. Overall, the discharge of active agents is made possible very selectively to the plant where a possibly unfavorable measurement result has been determined, so that a correspondingly low dosing of each agent is also possible.

The container for the controlled discharge of substances can be constructed for wrapping at least partially around the plant especially on a stem or stalk or branch. Therefore, it can be attached directly to the plant and in this way can be fixed so that it is hard for mechanical influences or small animals to reach or damage the container.

One improvement of the invention provides that the poles of the bipolar electrode in electrical contact with the plant are made from conductive plastic and project, in particular, in from the bipolar electrode on the inside of the coils. Thus, through the contact pressure force of the coils, for a certain play between the coil and stem it can also be ensured that in each case the poles of the bipolar electrode are brought into conductive contact with the attachment position of the plant. Conductive plastic is here advantageously corrosion resistant and thus can fulfill its function for a long time even under very unfavorable weather conditions.

The diameter of the double coil of the bipolar electrode and/or the distances of their windings can be adapted to the plant to be examined and the attachment position of this plant to be detected in its dimensions and in the applied spring force and spring hardness, which is possible very easily through the selection of such dimensions and the material that is used due to the very simple construction of the bipolar electrode with the double coil.

For the power supply of the amplifier, a public power main connection, a battery or accumulator connection, and/or at least one solar cell can be provided. Above all, one or more solar cells make the apparatus independent of power-supply lines, so that these can also be applied in fields and forests that are located at a large distance from houses or residential areas.

For good measurement results it is useful that the two or more poles of the bipolar electrode are arranged at positions of the double coil spaced apart from each other, in particular, on opposing windings of this double coil or twin coil.

For the assembly and handling of the apparatus, it is useful when the connections of the bipolar electrode are constructed as a plug for detachable connection to the memory or to the amplifier connected before the memory. The electrodes can then be mounted without a problem at the desired attachment positions of plants and can then be connected to the amplifier or the upstream memory optionally also via extension cables or the like. Above all, this arrangement also simplifies the connection of several electrodes to a common memory and/or amplifier.

Instead of the coil for mounting the bipolar electrode to a plant, for example, a foldable sleeve part or a clamp or the like could indeed also be provided, but a coil is preferred, because it is very flexible, the production and attachment are simple, and a practical, automatic adaptation of the coil to the growth of the attachment position of the plant can be realized.

BRIEF DESCRIPTION OF THE DRAWINGS

Below, embodiments of the invention are described in greater detail with reference to the drawing. Shown in partially schematized representation.

DETAILED DESCRIPTION OF THE PREFERRED EMBODIMENTS

Figure 1:
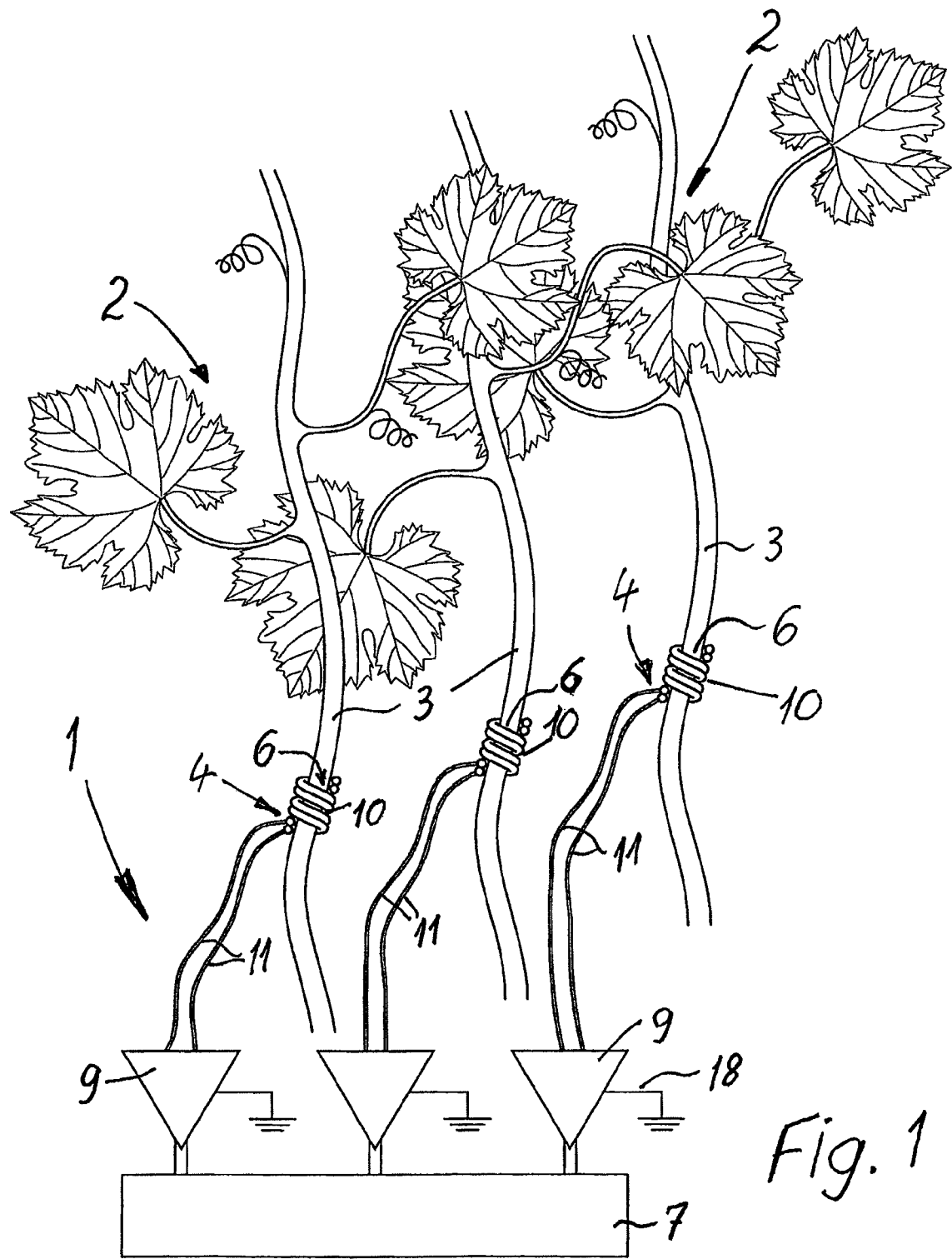
FIG. 1 an apparatus according to the invention for examining or monitoring the state of plants with, in this embodiment, three bipolar electrodes that are arranged on stems or stalks of grape vines using twin coils and that are connected to a memory through an amplifier, FIG. 2 at an enlarged scale, a bipolar electrode that includes the essential part of the apparatus according to the invention and whose two poles are arranged spaced apart from each other on the inside of a double coil from which the number of poles extend along two lines to plugs with which the different poles can be connected in a detachable manner to the amplifier and/or to the memory, FIG. 3 at an even further enlarged scale, the double coil with poles stripped on their inside, wherein it is indicated in a partial longitudinal section that the windings of the double coil are formed on their side by a coil made from thin wire or conductive material and are coated with insulation, so that the two coils of the double coil belonging to the different poles are also insulated from each other, FIG. 4 a top view of the double coil with a view on the poles projecting radially inward on the inside of the coil and made, for example, from electrically conductive plastic or metal for improving the contact with a plant stem, and FIG. 5 an apparatus according to the invention in which, in the area of the double coil, a container for the discharge of agents is provided that is controlled by the memory.

An apparatus designated as a whole with 1 (compare, in particular, FIG. 1 and FIG. 5) is used for examining or monitoring the state or state of health of plants 2, for example, grape vines, wherein damage due to environmental influences and/or pests can be determined during the growth or the life of such plants 2.

An essential part of the apparatus 1 is a bipolar electrode that can be attached at a position or to an area of the plant 2 where this plant outputs electrical signals and/or where an electrical potential is present or at a green position or to a green area of the plant 2, for example, a stem or stalk 3. This bipolar electrode is designated as a whole with 4 and can be seen especially well in FIG. 2. It has two poles 5 contacting the plant 2 in the position of use. According to FIG. 1 it surrounds the attachment positions 6 on the plant 2 in the position of use at least partially, in the shown embodiments, even completely, and receives electrical potentials or signals of the plant 2 via the poles 5, wherein the two poles 5 are spaced apart from each other.

The bipolar electrode 4 is connected to a detector or a memory 7 for detecting and evaluating these measurement results or potentials and for comparing potentials and signals received at different times. Here, in FIG. 2 one sees that the connections of the bipolar electrode 4 are constructed as a plug 8—for each pole 5 a plug—for detachable connection or attachment to the memory 7 or to an amplifier 9 connected before the memory 7. The bipolar electrode 4 can be connected detachably to the memory 7.

As already mentioned, between the attachment position 6 of the electrode 4 and the memory 7 there is an amplifier 9 that is here located between the electrode 4 or its connections 8 and the memory 7. In practice, the bipolar electrode 4 can be connected or is connected first to this amplifier 9 and only via this amplifier 9 to the memory 7. FIG. 1 makes it clear that several bipolar electrodes 4 are provided and connected to a common memory—advantageously each via an amplifier 9, in order to be able to simultaneously monitor a corresponding number of plants 2.

In a way not shown in greater detail, the memory 7 can be connected to an evaluation center wirelessly or via electrical lines or can even contain an evaluation apparatus itself. Thus, the measurement results can also be evaluated at a distance to the plants 2 and can trigger corresponding reactions, such as increased fertilization or spraying for pests with pesticides or the like.

As can be seen well in the figures, each bipolar electrode 4 has a holder or a holding end still to be described in greater detail for permanent and/or detachable attachment to each plant 2 and its attachment position 6. In the embodiments, this holder or the holding end of the electrode 4 is constructed for connecting to a plant 2 as a double coil or twin coil 10 with a line 11 leading from its common end to the plugs 8 or to the other connections on the memory 7 or the amplifier 9.

Figure 2:
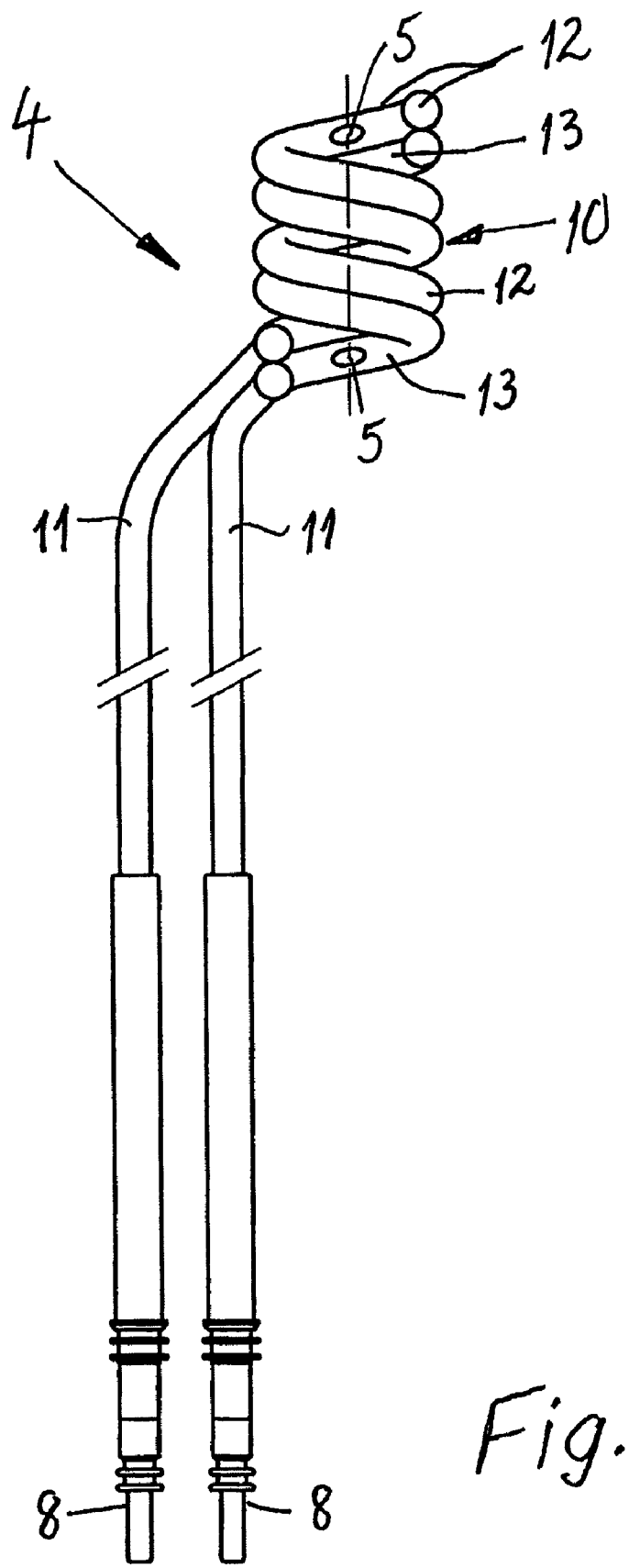

Each of the windings 12 and 13 with matching diameters and arranged parallel to each other carries or forms one of the poles 5 of the electrode 4, as can be seen well in FIGS. 2 and 3. Here it becomes clear that the pole 5 located on the winding 13 has the greatest possible distance from the pole 5 on the winding 12, wherein this distance corresponds approximately to the axial extension of the double coil or twin coil 10, in order to be able to perform a correspondingly clear measurement of each potential.

The double coil 10 here wraps around the measurement position and thus the attachment position 6 on the plant 2 on the entire extent of the stem 3, wherein the two coils according to FIG. 3 forming the windings 12 and 13 of the double coil 10 are insulated from each other and from the surroundings and have insulation-free or stripped contact positions as poles 5 for receiving the electrical potential of the plant 2 directly and/or for direct contact with the surrounded plant part 3 only at their area facing the plant part or stem 3 of the plant 2 and arranged in the interior of the double coil 10. The insulation is provided in FIG. 3 with the reference number 14 and can be, for example, silicon or rubber.

The bipolar electrode 4 and the holding and measurement coil, that is, the double coil 10, belonging to it are formed from a flexible and electrically conductive material, so that a good adaptation to the cross section and also to the growth of the attachment position 6 of the plant 2 is possible.

The two coils or windings 12 and 13 belonging to the bipolar electrode 4 are formed according to FIG. 3 on their side from wire coils 15 that extend within the insulation 14 and are formed according to FIG. 3 in the region of the holder on the plant 2 to the windings 12 and 13 of the double coil 10 that wraps around the plant 2 in the position of use at the attachment position 6. This leads to a very flexible arrangement that practically does not interfere with the plant and its movements and its growth and that has high flexibility and nevertheless good strength that also leads to a fixed connection to this position with practically no load on the attachment position 6.

The bipolar electrode 4 can be connected directly or indirectly to a controller that can be arranged in the embodiment, for example, within the memory 7 and with which, in particular, countermeasures specifically for the attack of pests, such as spraying of counteragents or pesticides or the discharge of fertilizer or the like can be triggered.

Figure 5:
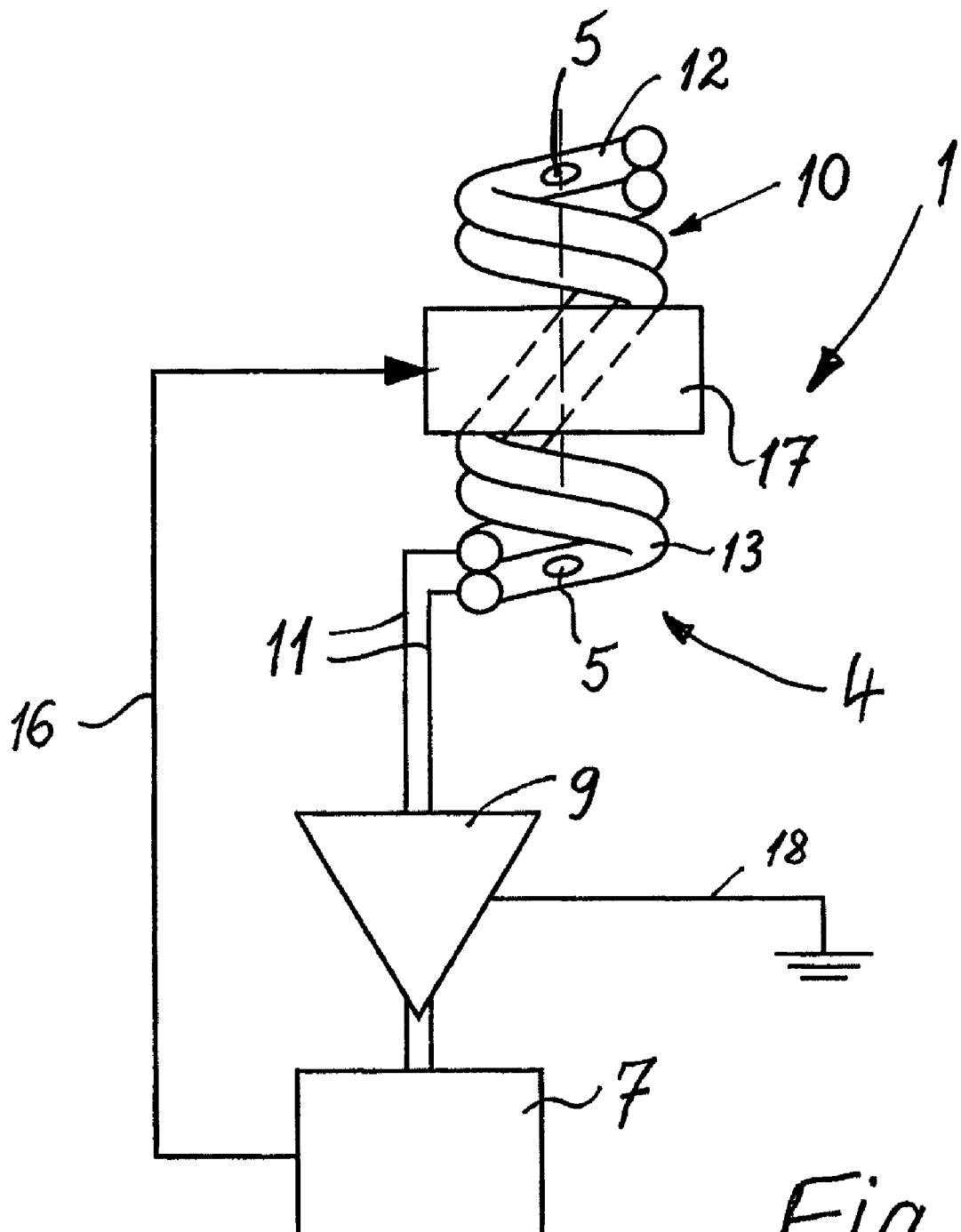

In FIG. 5, an embodiment is shown in which the memory 7 belonging to the apparatus 1 is connected to the controller arranged in it and therefore not shown separately and this is connected via a line 16, but can also be wireless, to a discharge apparatus or container 17 that contains corresponding countermeasures and has an initially closed or closable opening that can be opened by control pulses from the controller. Thus, according to the measurement of changing potentials, optionally even automatically, a targeted discharge of medicine, fertilizer, and/or pesticides from the container 17 can be provided. Here, the container 17 is shaped for the controlled discharge of countermeasures, medicine, or nutrients according to FIG. 5 so that it can attach to or by the attachment position 6 of the plant 2, where the electrode 4 also attaches, or can even by attached to it by the bipolar electrode 4 and its holder. The container 17 can also be constructed so that it partially surrounds the plant 2 at least partially, in particular, on a stem or stalk or branch 3. In a correspondingly targeted way, the contents of this container 17 can be used based on the measurements of the bipolar electrode 4.

In FIG. 4, on the double coil 10, radially projecting poles 5 can be seen in the interior that can be made from electrically conductive plastic and that can form an especially good contact with the plant 2 and its attachment position 6 due to its projection relative to the inner contours of the double coil 10. The use of electrically conductive plastic reduces corrosion problems, even though metallic poles 5 made from a corrosion-resistant metal could also be used.

In FIG. 1, one can see that the diameter of the double coil 10 of the bipolar electrode 4 is adapted to the plant 2 to be examined and the position 6 of this plant 2 to be gripped in its dimensions and also in the resulting spring force and hardness, in order to produce a fixed but detachable and adaptable attachment. In addition, the distances of the windings 12 and 13 and the material that is used can be preselected, in order to permit the most "inconspicuous" adaptation to a plant possible. Conversely, the electrode 4 can optionally also be used with the help of its double coil 10 for the support of a plant part that is otherwise too weak.

For powering the amplifier 9, a public power main connection, a battery or accumulator connection, and/or at least one solar cell can be provided, in order to also be able to monitor plant groups or fields or vineyards that are at a distance from typical power supplies accordingly. A corresponding power connection 18 is shown in FIG. 1.

The apparatus 1 is used for examining or monitoring the state or state of health of plants 2 with the help of a bipolar electrode 4 that taps corresponding potentials of the plant with its two or more different poles 5 and feeds these potentials to a detector and/or memory 7, in particular, via an amplifier 9, so that conclusions on the state or possible damage to a plant 2 can be drawn from changes in these electrical signals and remedial action can be taken.

The invention claimed is:

1. Apparatus (1) for examining or monitoring a state or state of health of plants (2) during growth or a life of such plants (2) the apparatus comprising a bipolar electrode (4) that is adapted to be attached to an attachment position (6) or to an area of the plant (2) where the bipolar electrode detects electrical signals or potentials output from the plant (2), the bipolar electrode has at least two poles (5) for contacting the plant (2) in a position of use, and the bipolar electrode wraps around the attachment position (6) on the plant (2) in the position of use at least partially or completely and are adapted to receive at least one of the electrical signals or potentials of the plant (2) and the bipolar electrode (4) is connected to at least one of a detector or a memory (7) for detecting and evaluating the electrical signals or potentials and for comparing the electrical signals or potentials received at different times, the bipolar electrode (4) has a holder or a holding end for attachment to the plant (2), the holder or the holding end of the electrode (4) is constructed for connection to the plant (2) as two coils arranged as a double coil or twin coil (10) having windings in which each of the windings (12, 13) arranged parallel to each other carries or forms one of the poles (5) of the electrode and the double coil (10) wraps around a measurement position on the plant (2) on an entire extent of the attachment position (6), and the two coils forming the double coil (10) are insulated from each other and from their surroundings and have insulation-free or stripped contact positions for receiving the electrical potential of the plant (2) directly or for direct contact with a surrounded plant part (3) on an area facing the plant part or stem of the plant arranged in an interior of the double coil (10).

2. Apparatus according to claim 1, wherein an amplifier (9) is provided between the attachment position (6) of the electrode (4) and the at least one of detector or the memory (7).

3. Apparatus according to claim 2, wherein for powering the amplifier (9) there is a connection for a public power main connection, a battery or accumulator, or at least one solar cell.

4. Apparatus according to claim 2, wherein the connections of the bipolar electrode (4) or associated lines thereof (11) are constructed as plugs (8) for detachable connection to the memory (7) or to the amplifier (9) connected before the memory (7).

5. Apparatus according to claim 1, wherein several bipolar electrodes (4) are provided and connected to a common memory (7).

6. Apparatus according to claim 5, wherein the memory (7) is connected to an evaluation center wirelessly or via electrical lines.

7. Apparatus according to claim 1, wherein the bipolar electrode (4) and the holding and measurement coil are formed from a flexible and electrically conductive material.

8. Apparatus according to claim 1, wherein the two coils (12, 13) belonging to the bipolar electrode (4) are formed from wire coils (15) that are formed in a region of the holder on the plant (2) into the windings (12, 13) of the double coil (10) that contacts or wraps around the plant (2) in the position of use.

9. Apparatus according to claim 1, wherein the bipolar electrode (4) is connected directly or indirectly to a controller with which countermeasures targeted to an attack by pests through spraying of counteragents or pesticides or a discharge of fertilizer can be triggered.

10. Apparatus according to claim 9, wherein the memory (7) of the apparatus is connected to the controller and this is connected to a discharge apparatus or container (17) that contains counteragents and has a closable opening that can be opened by control pulses from the controller.

11. Apparatus according to claim 10, wherein the container (17) is shaped for a controlled discharge of counteragents, medicine, or nutrients, and is adapted to be attached to the attachment position (6) of the plant (2) for the electrode (4) or can be fixed by the bipolar electrode (4) and its holder.

12. Apparatus according to claim 10, wherein the container (17) is constructed for the controlled discharge of substances for at least partially wrapping around the plant (2).

13. Apparatus according to claim 1, wherein the poles (5) of the bipolar electrode (4) in electrical contact with the plant are made from conductive plastic or corrosion-resistant metal and project out from the bipolar electrode (4) on an inside of the coil (10).

14. Apparatus according to claim 1, wherein a diameter of the double coil (10) of the bipolar electrode (4) or distances of the windings on the plant (2) to be examined and the position (6) of the plant (2) to be gripped are adapted in their dimensions to provide a resulting spring force and spring hardness.

15. Apparatus according to claim 1, wherein the two or more poles (5) of the bipolar electrode (4) are arranged at positions of the double coil (10) spaced apart from each other.

16. Apparatus according to claim 1, wherein diameters of the individual coils or the windings (12, 13) forming the double coil (10) are the same.

17. Apparatus according to claim 1, wherein at least one of silicon, rubber, goniomer, PE, or PUR is provided as a material for insulating the bipolar electrode (4) and the double coil or twin coil (10) or at least one of the windings or coils (12, 13).

* * * * *